United States Patent [19]

Thomas et al.

[11] Patent Number: 5,538,878
[45] Date of Patent: Jul. 23, 1996

[54] SUPEROXIDE DISMUTASE EXPRESSION IN PLANTS

[75] Inventors: Bruce Thomas; H. Maelor Davies; Jean Kridl; Jeffery K. O'Neal, all of Davis, Calif.; C. Jacques Van Assche, Marseille, France

[73] Assignees: Calgene, Inc., Davis, Calif.; Procida, Marseille, France

[21] Appl. No.: 381,827

[22] Filed: Jul. 19, 1989

Related U.S. Application Data

[63] Continuation-in-part of Ser. No. 265,049, Oct. 31, 1988, abandoned, which is a continuation-in-part of Ser. No. 229,639, Aug. 8, 1988, abandoned.

[51] Int. Cl.$^6$ .......................... C12N 15/31; C12N 15/53; C12N 15/82; A01H 5/00
[52] U.S. Cl. ..................... 435/172.3; 435/240.4; 435/320.1; 536/23.2; 536/23.6; 800/205; 935/64
[58] Field of Search ................... 536/23.2, 23.6; 800/205; 435/240.4, 320.1, 172.3; 935/64

[56] References Cited

U.S. PATENT DOCUMENTS 5,164,316  11/1992  McPherson et al. ................. 435/240.4

FOREIGN PATENT DOCUMENTS

| | | |
|---|---|---|
| 27461/84 | 11/1984 | Australia . |
| 0213628 | 3/1987 | European Pat. Off. . |
| 0359617 | 3/1990 | European Pat. Off. . |
| WO88/02402 | 4/1988 | WIPO . |

OTHER PUBLICATIONS

"Recombinant bacteria and plants for agriculture at AGS," *Genetic Technology News* (1986) vol. 6, No. 8, pp. 5, 8.
YEDA Res. & Dev. Co., Ltd., Derwent WPIL, Accession No. 84–312582; and AU–A–84 27 461 "abstract".
Shaalteil et al., "Biochemical analysis of paraquat resistance in Conyza leads to pinpointing synergists for oxidant generating herbicides", *Agrochemicals* (1987) 107:273, abstract No. 192885q.
Larson–Kelly et al., "Chloroplast Delivery of a Bacterial EPSP Synthase In Transgenic Plants and Tolerance to Glyphosate," *SAAS Bulletin Biochem. Biotech* (1988) 1:37–40.
Daniele Touati, "Cloning and Mapping of the Manganese Superoxide Dismutase Gene (sodA) of *Escherichia coli* K–12" *Journal of Bacteriology* (1983) 155 (3):1078–1087.
Guido Van Den Broeck et al., "Targeting of a Foreign Protein to Chloroplasts by Fusion to the Transit Peptide from the Small Subunit of Ribulose 1,5–Bisphosphate Carboxylase" *Nature* (1985) 313: Jan. 13, 1985.
Schreier et al., "The Use of Nuclear–Encoded Sequences to Direct the Light–Regulated Synthesis and Transport of a Foreign Protein into Plant Chloroplasts" *The EMBO Journal* (1985) 4: No. 1:25–32.
Lee et al., "Superoxide Dismutase" *Physiol. Plant*, (1982) 69:1444–1449.

Rabinowitch et al., "Photo–Oxidative Damage in the Ripening Tomato Fruit: Protective Role of Superoxide Dismutase" *Physiol. Plant* (1982) 54: No. 3:623–630.
Carlioz et al., "Isolation of Superoxide Dismutase Mutants in *Escherichia Coli*: Is Superoxide Dismutase Necessary for Aerobic Life?" *EMBO Journal* (1986) 5: No. 3:623–630.
Rabinowitch et al., "Superoxide Radicals, Superoxide Dismutases and Oxygen Toxicity in Plants" *Photochemistry and Photobiology* (1983) 37:679–690.
Bennet et al., "Biochemical Aspects of Plant Tolerance to Ozone and Oxyradicals: Superoxide Dismutase" *Plant Physiology Institute* Chapter 27 pp. 413–424.
Takeda and Avila, "Structure and gene expression of the *E. coli* Mn–superoxide dismutase gene", *Nucleic Acids Research* (1986) 14(11): 4577–4589.
Kwiatowski et al., "Isolation and characterization of an iron–containing superoxide dismutase from tomato leaves, *Lycopersicon esculentum*, " *Eur. J. Biochem.* (1985) 146:459–466.
Shah et al., "Engineering Herbicide Tolerance in Transgenic Plants," *Science* (1986) 233:478–481.
Bloch et al., "Paraquat–Mediated Selection for Mutations in the Manganese–Superoxide Dismutase Gene sodA," *Bacteriology* (1986) 168(2):795–798.
Elstner, "Oxygen Activation and Oxygen Toxicity," *Ann. Rev. Plant Physiol.* (1982) 33:72–96.
Sanders, et al., "Comparison of cauliflower mosaic virus 35S and nopaline synthase promoters in transgenic plants," *Nucleic Acids Research* (1987) 15(4): 1543–1558.
Hassan and Fridovich, "Paraquat and *Escherichia coli*: Mechanism of Production of Extracellular Superoxide Radical," *The Journal of Biological Chemistry* (1979) 254(21):10846–10852.
Kuntz et al., "Targeting of protein to chloroplasts in transgenic tobacco by fusion to mutated transit peptide," *Mol. Gen. Genet.* (1986) 205:454–460.
Karlin–Neumann and Tobin, "Transit peptides of nuclear–encoded chloroplast proteins share a common amino acid framework," *The EMBO Journal* (1986) 5:9–13.
Wasmann et al., "The importance of the transit peptide and the transported protein for protein import into chloroplasts," *Mol. Gen. Genet.* (1986) 205:446–453.
Flurh et al., "Expression dynamics of the pea rbcS multigene gamily and organ distribution of the transcripts," *The EMBO Journal* (1986) 5(9):2063–2071.
Facciotti et al., "Light–inducible expression of a chimeric gene in soybean tissue transformed with *agrobacterium*," *Bio/Technology* (1985) 3:241–246.

(List continued on next page.)

*Primary Examiner*—Patricia R. Moody
*Attorney, Agent, or Firm*—Barbara Rae-Venter

[57] ABSTRACT

Plant species having enhanced superoxide dismutase activity as a result of transformation with a DNA expression cassette comprising an *E. coli* MnSOD gene are provided. Transportation of the expression product of the gene may be targeted to a specific cell organelle, such as the chloroplast.

33 Claims, 2 Drawing Sheets

OTHER PUBLICATIONS

Berry–Lowe et al., "The Nucleotide Sequence, Expression, and Evolution of One Member of a Multigene Family Encoding the Small Subunit of Ribulose–1,5–Bisphosphate Carboxylase in Soybean," *Journal of Molecular and Applied Genetics* (1982) 1(6):483–498.

O'Neal et al., "Isolation of tobacco SSU genes: characterization of a transcriptionally active pseudogene," *Nucleic Acids Research* (1987) 15:8661–8677.

Palma et al., "Increased Levels of Peroxisomal Active Oxygen–Related Enzymes in Copper–Tolerant Pea Plants," *Plant Physiol.* (1987) 85:570–574.

Tepperman et al 1990 Pl Molec Biol 14:501–511.

Perl et al 1993 Theoretical & Applied Genetics 85:568–576.

Kelner et al 1990 The Journal of Biological Chemistry 265(19): 10872–10875.

Kay et al 1987 (5 Jun.) Science 236: 1299–1302.

SUPEROXIDE DISMUTASE EXPRESSION IN PLANTS

CROSS-REFERENCE TO RELATED APPLICATIONS

This application is a continuation in part of U.S. application Ser. No. 265,049 filed Oct. 31, 1988, now abandoned, which is a continuation-in-part of U.S. application Ser. No. 229,639, filed Aug. 8, 1988, now abandoned which application is hereby incorporated herein by reference.

INTRODUCTION

1. Technical Field

This invention relates to plants, and methods for their preparation, having increased tolerance to environmental and chemical stresses. The method employs transformation of the plants so as to increase the concentration of superoxide dismutase in the plant's cells, especially in the chloroplasts.

2. Background

In plants, as in other aerobic organisms, superoxide ($O_2^-$) is a commonly encountered intermediate of oxygen reduction. Superoxide is extremely toxic to cells because it attacks unsaturated fatty acid components of membrane lipids, thus damaging membrane structure. Aerobic cells detoxify superoxide by the action of superoxide dismutases, metal-containing enzymes that convert the superoxide radical into hydrogen peroxide and molecular oxygen. The hydrogen peroxide is subsequently converted by catalase into water and molecular oxygen. Superoxide dismutases thus provide a defense against the potential cytotoxicity of the superoxide radical.

There are three types of superoxide dismutase (SOD): copper/zinc-containing SOD (CuZnSOD), manganese-containing SOD (MnSOD) and iron-containing SOD (FeSOD). All three types of SOD have been found in plants. CuZn-SODs are inhibited by cyanide, while FeSODs and MnSODs are not. In prokaryotic organisms containing both Mn and FeSODs, MnSOD is inducible under conditions of high oxygen concentration and by $O_2^-$, while FeSOD is constitutively expressed. In plants, CuZnSOD and FeSOD are feedback inhibited by $H_2O_2$; MnSOD is not. MnSODs are usually localized within mitochondria. In leaves and fruit of most plants examined, MnSOD represents only 3–5% of total SOD activity although it can be as high as 20% in, for example, peas. FeSOD has been found in only a few families of seed plants where it may have arisen by gene transfer from prokaryotes.

Induction of superoxide dismutase activity in plant cells has been correlated with development of increased tolerance to a variety of chemical compounds and physical stresses. Plants which show resistance to herbicides such as paraquat contain more total SOD activity in a number of tissues, including fruit and leaves, than the corresponding paraquat-sensitive genotypes. Tolerance to toxic gases (for example, ozone, sulfur dioxide), metals (for example, copper, iron, zinc and manganese) and damage due to environmental stresses such as photodynamic processes and thermal effects such as sun scald have also been correlated with increased levels of SOD activity.

Environmental stresses are considered to decrease crop productivity to various extents, depending upon the severity of and the type of stress. Enhancing the tolerance of crop plants to adverse effects imposed by nonoptimal growing conditions is thus an important objective for improvement of crop management. There is therefore substantial interest in the ability to increase the concentration of superoxide dismutase in a plant cell so as to provide for a plant which has increased tolerance to environmental and chemical stresses.

Relevant Literature

The gene for manganese superoxide dismutase from *Escherichia coli* K-12 has been cloned. Touati, *J. Bacteriol.* (1983) 155:1078–1087. The DNA sequence of the *E. coli* K-12 manganese superoxide dismutase gene has been determined. Takeda et al., *Nucleic Acids Research* (1986) 14:4577–4589. The amino acid sequence of *E. coli* B manganese superoxide dismutase is known. Steinman, *J. Biol. Chem.* (1978) 253:8708–8720. The cDNA clones of two CuZnSODs from tomato are disclosed in Perl-Treves et al., *Plant Molecular Biology* (1988) 11:609–623.

The use of a transit peptide of pea small subunit (ssu) ribulose-1,5-bisphosphate carboxylase fused to an exogenous gene to provide a chimeric gene has been disclosed for targeting a heterologous gene product to chloroplasts. See, for example, Van den Broeck et al., *Nature* (1985) 313:358–363; Schreier et al., *EMBO J.* (1985) 4:25–32.

A possible protective role for superoxide dismutase against ozone injury in snap beans has been reported by Lee et al., *Plant Physiol.* (1982) 69:1444–1449. The effect of SOD defense against $SO_2$ toxicity was described by Tanaka et al., *Plant and Cell Physiol.* (1980) 21:601–611. Similarly a protective role for superoxide dismutase against photooxidative damage in the ripening tomato fruit has been reported. Rabinowitch et al., *Physiol. Plant.* (1982) 54:369–374. Superoxide dismutase minus mutants of *E. coli* are disclosed as having increased sensitivity to paraquat and to oxygen. Carlioz and Touati, *EMBO J.* (1986) 5:623–630. The role of SOD in drought tolerance of mosses was reported by Dhindsa and Matowe, *Exp. Botany* (1981) 32:79–91.

Treatment of soybeans with iron and/or manganese is reported to affect total SOD activity; MnSOD activity is reported to be modified only by manganese concentrations. Leidi et al., *Plant and Soil* (1987) 99:139–146. Palma et al., *Plant Physiol.* (1987) 85:570–577 disclosed that there is no change in mitochondrial SOD activity but that there is increased peroxisomal Mn-SOD activity in Cu-tolerant as compared to Cu-sensitive plants. Bowler et al., *EMBO* (1988) 8:31–38 disclosed an increase in SOD mRNA following exposure of a plant to ethylene, salicylic acid and infection with *Pseudomonas syringae*.

Characterization of FeSOD from tomato was described by Kuiakowski et al., *Eur. Biochem.* (1985) 146:459–466. The following review article is related to superoxide dismutase in plants: Rabinowitch et al., *Photochemistry and Photobiology* (1983) 37:679–690.

SUMMARY OF THE INVENTION

Novel plants, and methods for their preparation, are provided which have enhanced superoxide dismutase activity. The plants are regenerated from cells transformed using expression cassettes comprising a DNA sequence encoding superoxide dismutase attached to a plant promoter. The DNA can additionally be attached to chloroplast leader sequences for delivery to and expression in the plant chloroplast. The expression cassettes are introduced into the plant cell host for integration into the genome so that enhanced activity of superoxide dismutase is achieved in the plant cell of interest, especially in the chloroplast.

DESCRIPTION OF THE SPECIFIC EMBODIMENTS

Figure 1A:
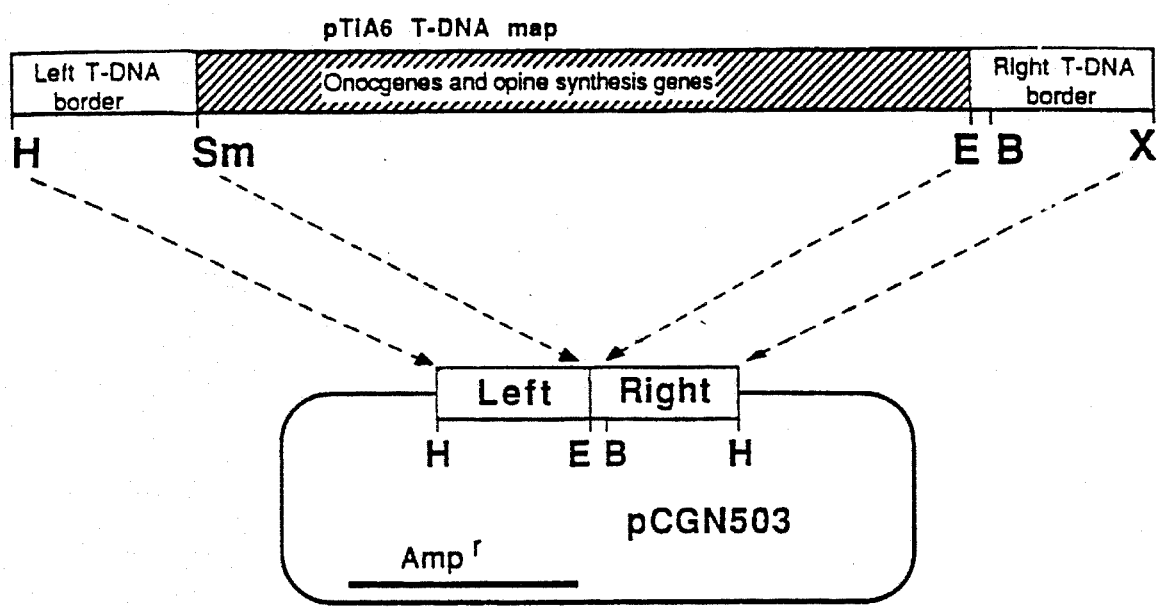
FIGS. 1A through 1G shows the construction of disarmed Agrobacterium K61.
Figure 1B:
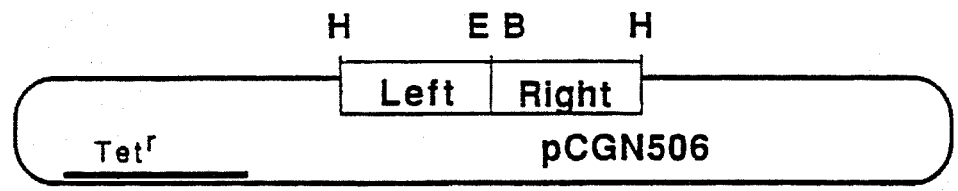
Figure 1C:
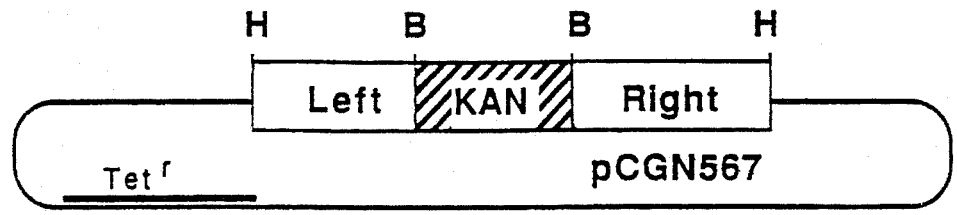
Figure 1D:
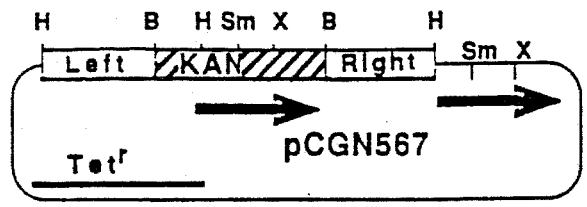

In accordance with the subject invention, methods and compositions are provided which allow for modification of superoxide dismutase activity in plants. Plant cells are transformed using expression cassettes having transcriptional and translational regulatory sequences functional in a plant cell and an open reading frame encoding a heterologous or homologous superoxide dismutase under the transcriptional and translational control of the regulatory regions. The translation of an inserted superoxide dismutase DNA sequence will augment levels of superoxide dismutase already present in the cell. Thus, the presence of the superoxide dismutase resulting from transcription and translation of the added DNA sequence will increase the concentration of superoxide dismutase in the plant cell. The open reading frame also can include a DNA sequence encoding a transit peptide recognized by the plant host and post-processing N-terminal amino acids from a mature protein which provides for targeting of the superoxide dismutase into a cell organelle.

The introduction of polypeptides into a cell organelle such as a chloroplast or mitochondria is achieved by joining a DNA sequence coding for the transit peptide in reading frame with a sequence encoding a structural gene for superoxide dismutase. When expressed, the fused transit peptide/superoxide dismutase protein will be cleaved by the cell organelle for the introduction of the superoxide dismutase enzyme into the organelle. In a first embodiment, the transit peptide and the superoxide dismutase protein are fused directly to one another. In a second preferred embodiment, the transit peptide and the superoxide dismutase protein are linked together via a glutamate amino acid. In a third embodiment, the transit peptide and the superoxide dismutase are joined together by about 1–30 post processing amino acids of the N-terminus of a mature, ribulose biphosphate carboxylase (RuBPcase) ssu polypeptide. The expression cassette will thus include in the 5'-3' direction of transcription, a transcriptional and translational initiation region functional in a plant cell; a structural gene encoding superoxide dismutase, preferably including in reading frame a sequence encoding a transit peptide, wherein said transit peptide directs transfer of the superoxide dismutase to a plant cell organelle; and a transcriptional and translational termination regulatory region. The initiation and termination regulatory regions are functional in a plant cell and provide for efficient expression of the superoxide dismutase with desirable effects on the viability and proliferation of the plant host.

The superoxide dismutase DNA sequence may be native to the plant host or heterologous, and may be derived from prokaryotic or eukaryotic sources. Prokaryotic sources are preferred. The structural gene for the superoxide dismutase may be obtained in a variety of ways. The gene may be synthesized in whole or in part, particularly where it is desirable to provide plant preferred codons. Thus, all or a portion of the open reading frame may be synthesized using codons preferred by the plant host. Plant preferred codons may be determined from the codons of highest frequency in the proteins expressed in the largest amount in the particular plant species of interest.

Methods for synthesizing sequences and bringing the sequences together are well established in the literature. Where a portion of the open reading frame is synthesized, and a portion is derived from natural sources, the synthesized portion may serve as a bridge between two naturally occurring portions, or may provide a 3'-terminus or a 5'-terminus. Particularly where the transit peptide and the open reading frame encoding the superoxide dismutase are derived from different genes, synthetic adapters commonly will be employed. In other instances, linkers may be employed, where the various fragments may be inserted at different restriction sites or substituted for a sequence in the linker.

For the most part, some or all of the super-oxide dismutase structural gene will be from a natural source and is preferentially E. coli MnSOD, since this enzyme is not feedback inhibited by hydrogen peroxide. Methods for identifying sequences of interest have found extensive exemplification in the literature, although in individual situations, different degrees of difficulty may be encountered. Various techniques include the use of probes where genomic or cDNA libraries may be searched for complementary sequences.

When the structural gene to be inserted is derived from, for example, bacterial MnSOD, it may be desirable to eliminate a large portion of the 3' non-coding region of the bacterial gene. Thus, in some instances, a truncated gene may be employed, where up to 0.8 kb of the bacterial 3' untranslated region of MnSOD may be removed. Elimination of this untranslated region may have a positive effect on the transcription, stability, and/or translation of the mRNA in the plant cells.

The transcriptional and translational initiation regulatory regions may be homologous or heterologous to the plant host. Of particular interest are transcriptional initiation regions from genes which are present in the plant host or other plant species, for example, the tobacco ribulose biphosphate carboxylase ssu transcriptional initiation region; those present in viruses such as the cauliflower mosaic virus (CaMV) 35S transcriptional initiation region, including a "double" 35S CaMV promoter ("MAC") described in co-pending U.S. application Ser. No. 339,755 filed Apr. 18, 1988; and those associated with T-DNA, such as the opine synthase transcriptional initiation region, e.g., octopine, mannopine, agropine, and the like.

Any one of a number of regulatory sequences may be preferred in a particular situation, depending upon whether constitutive or induced transcription is desired, the particular efficiency of the promoter in conjunction with the heterologous superoxide dismutase, the ability to join a strong promoter with a control region from a different promoter which allows for inducible transcription, ease of construction and the like. These regulatory regions find ample precedence in the literature.

Transport of the heterologous superoxide dismutase into other cellular compartments may be accomplished by the use of a transit peptide to target a desired cellular compartment such as a chloroplast. The transit peptide may be from the same gene as the transcriptional initiation regulatory region and/or the host organism or from a gene foreign to both the transcriptional initiation region and the host organism.

Of particular interest is the use of a transit peptide which provides for transport of the superoxide dismutase to a plant cell chloroplast or mitochondria. Otherwise, the superoxide dismutase expressed in the transgenic plant will be found in the cytoplasm. Transit peptides which may be employed can be obtained from genes encoding chloroplast proteins produced in the cytoplasm, then translocated to the chloroplast. Such proteins include tobacco and soybean ribulose biphosphate carboxylase ssu, acyl carrier protein (ACP), chlorophyll A/B binding protein and other components of fatty acid synthesis.

To enhance the efficiency of transport, a DNA sequence encoding the transit peptide can be fused in reading frame with a DNA sequence encoding a peptide comprising post-processing N-terminal amino acids of a nuclear-encoded chloroplast protein such as the mature ribulose biphosphate carboxylase ssu polypeptide from pea. The optimum number of post-processing amino acids will generally be 10 to 30, preferably 10 to 20 amino acids. The DNA sequence is generally inserted at the border between the 3' end of the transit peptide sequence and the 5' end of the superoxide dismutase gene. It may be inserted directly if a convenient restriction site is available, or a synthetic restriction site can be created at the 3'-5' border. One or more amino acids can be added to the 5' end of the SOD coding region. In the most preferred mode, a glutamine is added to the SOD. In other, less preferred embodiments, the additional glutamine codon may be removed by techniques known in the art, and replaced with a codon(s) for other amino acid(s). Methods for preparing chimeric genes comprising transit peptides and post-processing amino acids include those described in copending U.S. application Ser. No. 912,408 filed Sep. 26, 1986, which disclosure is hereby incorporated by reference.

The termination region may be derived from the 3'-region of the gene from which the initiation region was obtained or from a different gene. Preferably the termination region will be derived from a plant gene, particularly the tobacco ribulose biphosphate carboxylase ssu termination region; a gene associated with the Ti-plasmid such as the octopine synthase termination region; or the tml termination region.

In developing the expression cassette, the various fragments comprising the regulatory regions and open reading frame may be subjected to different processing conditions, such as ligation, restriction, resection, in vitro mutagenesis, primer repair, use of linkers and adapters, and the like. Thus, nucleotide transitions, transversions, insertions, deletions, or the like, may be performed on the DNA which is employed in the regulatory regions and/or open reading frame.

During the construction of the expression cassette, the various fragments of the DNA will usually be cloned in an appropriate cloning vector, which allows for amplification of the DNA, modification of the DNA or manipulation by joining or removing of the sequences, linkers, or the like. Normally, the vectors will be capable of replication in at least a relatively high copy number in *E. coli*. A number of vectors are readily available for cloning, including such vectors as pBR322, pUC series, M13 series, etc. The cloning vector will have one or more markers which provide for selection of transformants. The markers will normally provide for resistance to cytotoxic agents such as antibiotics, heavy metals, toxins, or the like. By appropriate restriction of the vector and cassette, and as appropriate, modification of the ends, by chewing back or filling in overhangs, to provide for blunt ends, by addition of linkers, by tailing, complementary ends can be provided for ligation and joining of the vector to the expression cassette or component thereof.

After each manipulation of the DNA in the development of the cassette, the plasmid will be cloned and isolated and, as required, the particular cassette component analyzed as to its sequence to ensure that the proper sequence has been obtained. Depending upon the nature of the manipulation, the desired sequence may be excised from the plasmid and introduced into a different vector or the plasmid may be restricted and the expression cassette component manipulated, as appropriate.

The manner of transformation of *E. coli* with the various DNA constructs (plasmids and viruses) for cloning is not critical to this invention. Conjugation, transduction, transfection or transformation, for example, calcium phosphate mediated transformation, may be employed.

In addition to the expression cassette, depending upon the manner of introduction of the expression cassette into the plant cell, other DNA sequences may be required. For example when using the Ti- or Ri-plasmid for transformation of plant cells, as described below, at least the right border and frequently both the right and left borders of the T-DNA of the Ti- or Ri-plasmids will be joined as flanking regions to the expression cassette. The use of T-DNA for transformation of plant cells has received extensive study and is amply described in *Genetic Engineering, Principles and Methods* (1984) Vol 6 (Eds. Setlow and Hollaender) pp. 253–278 [Plenum, N.Y.]; A. Hoekema, in: *The Binary Plant Vector System* (1985) Offsetdrukkerij Kanters, B. V. Alblasserdam.

Alternatively, to enhance integration into the plant genome, terminal repeats of transposons may be used as borders in conjunction with a transposase. In this situation, expression of the transposase should be inducible, so that once the expression cassette is integrated into the genome, it should be relatively stably integrated and avoid hopping.

The expression cassette will normally be joined to a marker for selection in plant cells. Conveniently, the marker may be resistance to a biocide, particularly an antibiotic, such as Kanamycin, G418, Bleomycin, Hygromycin, Chloramphenicol, or the like. The particular marker employed will be one which will allow for selection of transformed plant cells as compared to plant cells lacking the DNA which has been introduced.

A variety of techniques are available for the introduction of DNA into a plant cell host. These techniques include transformation with Ti-DNA employing *A. tumefaciens* or *A. rhizogenes* as the transforming agent, protoplast fusion, injection, electroporation, DNA particle bombardment, and the like. For transformation with agrobacterium, plasmids can be prepared in *E. coli* which plasmids contain DNA homologous with the Ti-plasmid, particularly T-DNA. The plasmid may be capable of replication in agrobacterium, by inclusion of a broad spectrum prokaryotic replication system, for example RK290, if it is desired to retain the expression cassette on an independent plasmid rather than having it integrated into the Ti-plasmid. By means of a helper plasmid, the expression cassette may be transferred to the *A. tumefaciens* and the resulting transformed organism used for transforming plant cells. The plant cells may be any photosynthetic plant cells, or other cells in which elevated concentrations of the superoxide radical are produced.

Conveniently, explants may be cultivated with the *A. tumefaciens* or *A. rhizogenes* to allow for transfer of the expression cassette to the plant cells, the plant cells dispersed in an appropriate selection medium. The agrobacterium host will contain a plasmid having the vir genes necessary for transfer.

After transformation, the cell tissue (for example protoplasts, explants or cotyledons) is transferred to a regeneration medium, such as Murashige-Skoog (MS) medium for plant tissue and cell culture, for formation of a callus. Cells which have been transformed may be grown into plants in accordance with conventional ways. See, for example, McCormick et al., *Plant Cell Reports* (1986) 5:81–84. The transformed plants may then be analyzed to determine whether the desired gene product is still being produced in all or a portion of the plant cells. After expression of the desired product has been demonstrated in the plant, the plant can be grown, and either pollinated with the same transformed strain or different strains and the resulting hybrid having the desired phenotypic characteristic identified. Two or more generations may be grown to ensure that the subject phenotypic characteristic is stably maintained and inherited.

Various techniques exist for determining whether the desired DNA sequences are present in the plant cell and are being transcribed. Techniques such as the Northern blot can be employed for detecting messenger RNA which codes for MnSOD. In addition, the presence of expression can be detected in a variety of ways. The expression of MnSOD in transformed plants may be detected by several means including solution enzyme assay, Western analysis and native electrophoresis with activity staining. Furthermore, antibodies specific for mature MnSOD may be employed.

The response of the transformed plants to various stresses such as high or low (chilling) temperature, water deficit, high metal content of the rhizosphere, exposure to herbicides such as paraquat dichloride (1,1-dimethyl-4,4-bipyridilium dichloride), salinity or conditions favoring photooxidative damage or photoinhibition can be measured in a variety of ways. The stress one of the above factors alone, or in combination with at least one other factor; or with high light intensity.

The transgenic plants can be evaluated directly, for example, transgenic plants can be evaluated for tolerance/resistance particularly to chemical stresses such as herbicides and metals, by the ability of the plant to grow in the presence of higher concentrations of the toxic compound as compared to non-transgenic plants, or plants transformed with other than an expression cassette providing for increased SOD activity.

Exposure of plants to stress conditions (see relevant review from S. Powles (1984) Annual Review of Plant Physiology, 35; 15–44) results in inhibition of photosynthesis. Thus the effects of oxygen toxicity and photoinhibition are strongly directed towards photosynthesis. Under normal, physiological conditions, photosynthesis is defined as the vectorial photosynthetic electron transport (P.E.T.) and the subsequent $CO_2$ reduction. The relatively high susceptibility of photosystem II is frequently related to a loss of chlorophyll variable fluorescence. Since P.E.T. is affected by various stresses it can be used for "in situ" evaluation of the stress resistance of the transgenic plants.

Plants engineered to produce increased levels of SOD activity in response to environmental stresses find use in being able to grow under conditions which inhibit growth of the parental strain, in particular under conditions which increase plant superoxide ($O_2^-$) to growth inhibitory levels. Examples of such conditions include increased salinity, drought and elevated metal concentration of the rhizosphere. These plants may also find use where it is desirable to use herbicides such as the salts of bipyridylium quaternary ammonium compounds, for example paraquat, for weed control.

Evaluation of the amount of SOD activity in the transgenic plants may also be used as an indicator of nutritional deficiency of the soil, an increase reflecting a stress-inducing deficiency. Thus, the plants themselves may find use as indicator crops for presence of undesirable components in the soil or absence of desirable nutrients where the desirable or undesirable components affect SOD activity. The relatively large response to environmental stress due to increased copy number of the SOD gene and the use of an inducible enzyme (e.g. MnSOD), provide for a substantially more reliable indication than can be obtained using standard plants.

The following examples are offered by way of illustration and not by way of limitation.

EXPERIMENTAL

Standard laboratory techniques of restriction, ligation, transformation, and analysis (Maniatis et al., (1982) Molecular Cloning: A Laboratory Manual, Cold Spring Harbor Laboratory, New York) were used. Single-stranded DNA template was prepared and DNA sequence was determined using the Sanger dideoxy technique (Sanger et al., *Proc. Nat'l. Acad. Sci. USA* (1977) 74: 5463–5467). Double-stranded DNA was sequenced using the technique of Maxam and Gilbert (1980) Methods Enzymol. 65:499–560). Sequence analysis was performed using a software package from IntelliGenetics, Inc.

Cloning vectors used include pUC vectors, pUC8 and pUC9 (Vieira and Messing, *Gene* (1982) 19:259–268), pUC18 and pUC19 (Norrander et al., *Gene* (1983) 26:101–106; Yanisch-Perron et al., *Gene* (1985) 33:103–119), and analogous vectors exchanging chloramphenicol resistance (CAM) as a marker for the ampicillin resistance of the pUC plasmids described above (pUC-CAM [pUC12-Cm, pUC13-Cm] Buckley, K., Ph.D. Thesis, U.C.S.D., CA 1985). The multiple cloning sites of pUC18 and pUC19 vectors were exchanged with those of pUC-CAM to create pCGN565 and pCGN566 which are CAM resistant. Phage vectors used included M13mp8 and M13mp9 (Messing and Vieira, *Gene* (1982) 19, 269–276 and M13mp18 and M13mp19 (Norrander et al., supra; Yanish-Perron et al., supra).

EXAMPLE 1

Superoxide Dismutase Purification and Antibody Production

Manganese superoxide dismutase (MnSOD) was purified from *E. coli* B which had been grown under conditions designed to induce production of the enzyme (100 μM $FeSO_4 \cdot 7H2O$, 100 μM $MnSO_4$, 100 μM 8-hydroxyquinoline, 10 μM methylviologen). The purification scheme was based on that of Keele et al., *J. Biol. Chem.* (1970) 245:6176–6181. Enzyme activity was monitored based on the assay described by Misra et al., *Arch. Biochem. Biophys.* (1977) 181:308–312. The purified enzyme was lyophilized and used for antibody production. Since there may be cross-reactivity between the antibody prepared against the bacterial MnSOD and that present in chloroplasts, the plant and bacterial MnSOD for Western blotting are separated on an isoelectric focusing gel or using a normal SDS-gel system.

Briefly, intact chloroplasts were isolated from tobacco leaves using an isolation protocol as described by Jensen et al., *Proc. Nat'l. Acad. Sci. USA* (1966) 56:1095–1101. The chloroplasts were osmotically lysed by resuspending in extraction buffer containing 100 mM sodium citrate, pH 5.5, 10 mM EDTA, 150 mM NaCl, 0.05% (v/v) Nonident P-40, 25 mg/ml BSA, 1 mM DTT, 10 mM thiourea, 10 μM leupeptin. The samples were then subjected to immunoprecipitation of cross-reacting proteins using the antiserum to the purified bacterial SOD as follows. To 1 ml of the supernatant liquid was added 25 μl of antiserum and 125 μl *S. aureus* (freeze dried cells). The samples were incubated at room temperature for 45 minutes, centrifuged at 3000×g for 5 minutes and the pellet washed twice with 20 mM Tris pH 7.5, 1 mM EDTA, 50 mM NaCl and 0.05% (v/v) Nonident P-40. The precipitated protein was resuspended and denatured in electrophoresis sample buffer, (Anderson and Anderson, *Proc. Nat'l. Acad. Sci. USA* (1977) 74:5421–5425) containing 2% (w/v) SDS, 2% (v/v) Triton X-100, 5% (v/v) mercaptoethanol, 20% (v/v) glycerol and 2% (w/v) LKB Ampholines (pH 3.5–10). To one sample was added 0.5 μg of purified MnSOD from *E. coli*. In the isoelectric focusing gel method, samples were then subjected to isoelectric focusing in 9 M urea at 500 v in a 1.5 mm thick 4.25% polyacrylamide gel (5.7% cross-linked, pH 3.5–10) at 0° C. for 18 hours, otherwise the samples were separated using typical SDS-PAGE system for Westerns as discussed in Example 8.

The resolved proteins were transferred to nitrocellulose (BA 85 Schleicher and Schuell) as described by Burnette (*Anal. Biochem.* (1981) 112:195–203) at 100 v for three hours in a Hoefer TE42 transfer unit. The nitrocellulose filter was then incubated in Blotto for 1 hour at room temperature followed by an overnight incubation at 4° C. in 50:1 Blotto:antiserum. The filter was washed for 10 minutes in 20 mM Tris, pH 7.5, 150 mM NaCl, for 20 minutes in the same buffer containing 0.05% Tween-20 and for another 10 minutes in buffer without detergent. Blotto containing $10^6$ cpm/ml of $^{125}$I-labeled protein A (9 μCi/mg; NEN) was then added to the filter and incubated at room temperature for two hours. The filter was then washed overnight in 50 mM Tris, pH 7.5, 1M NaCl and 0.4% (w/v) Sarkosyl. After rinsing and drying, filters were exposed for 24 hours to Kodak XAR x-ray film at –70° C. using a DuPont Cronex intensifying screen.

EXAMPLE 2

Subcloning and Sequencing of the MnSOD Gene

A MnSOD gene (sodA) from *E. coli* K12 was obtained from Danielle Touati on plasmid pDT1-5 (Touati, *J. Bacteriol.* (1983) 155: 1078–1087). The plasmid contained a 4.8 kb EcoRI, BamHI fragment of *E. coli* genomic DNA. The SOD gene nucleotide sequence has been published (Takeda and Avila, *Nucl. Acids Res.* (1986) 14:4577–4589). A nucleotide sequence independently derived at Calgene from pDT1-5 is identical to that reported except for a C residue in place of the published T at the third nucleotide of codon #58. This creates an additional BclI restriction site. A 3.5 kb HincII/BamHI fragment of pDT1-5 was subcloned to M13mp8 cut with BamHI and SmaI to create pCGN1300a.

EXAMPLE 3

Creation of an SphI Site for Insertion of a Chloroplast Leader Sequence

Construction of pCGN1303

Single-stranded DNA from clone pCGN1300a was subjected to in vitro mutagenesis (Adelman et al., *DNA* (1983) 2:183–193) to insert a SphI site at the initiation codon of the MnSOD gene. The synthesized 35 base oligonucleotide 5'-GCAGGGTATAGCTCTGCATGCATTGTCGGGCGCCA-3'. After in vitro mutagenesis, one clone pCGN1303 was selected and the sequence of the mutated region was confirmed by both Maxam and Gilbert sequencing from the NcoI site 68 nucleotides from the SOD start codon and by subcloning the SphI-BamHI fragment of pCGN1303 into M13 and subsequent Sanger dideoxy sequencing. The in vitro mutagenesis to add the SphI site to the 5'-end of SOD added one amino acid (glutamine) to the coding region.

Expression of Altered MnSOD in an SOD⁻ Mutant

To investigate the effect of the extra amino acid on SOD activity, the EcoRI-HindIII fragment of pCGN1303 containing the SOD gene and its own promoter was transferred from its M13mp8 background to pUC19 that had been digested with EcoRI and HindIII to give pCGN1309. pCGN1309 was then used to transform an SOD⁻ *E. coli* strain similar to the double mutant (MnSOD⁻ and FeSOD⁻) described by Carlioz and Touati, *EMBO J.* (1986) 5:623–630. SOD activity was detected in the pCGN1309-transformed SOD⁻ cells by electrophoresis of extracts prepared as described by Touati, *J. Bacteriol.* (1983) 155:1078–1087 on non-denaturing polyacrylamide gels and staining for activity (Beauchamp and Fridovich, *Anal. Biochem.* (1971) 44:276–287). No detectable activity was seen in SOD⁻ cells alone or when transformed with pUC19. SOD⁻ cells transformed with pCGN1309 showed approximately the same amount of activity, 1 unit/30 μg of total protein, as *E. coli* 7118 cells (Messing et al., *Proc. Nat'l. Acad. Sci. USA* (1977) 74:3642–3646).

EXAMPLE 4

MnSOD Expression Constructs for Chloroplast Targeting

Both plant gene expression signals (promoter and 3'-sequences) and a leader sequence must be added to the bacterial MnSOD gene to have the gene product expressed and transported to plant chloroplasts. A binary vector, named pCGN1332, containing a tobacco ssu ribulose bisphosphate carboxylase (RuBPcase) promoter and leader sequences, the MnSOD gene and tobacco ssu 3'-regulatory sequences with a plant selectable kanamycin resistance marker, was constructed as follows: A 3.4 kb EcoRI fragment of lambda clone TSSU3-8 (O'Neal et al., *Nucl. Acids Res.* (1987) 15:8661–8677 containing a ssu RuBPCase gene from tobacco was subcloned into M13mp18 digested with EcoRI to give plasmid 2018. The promoter and leader of the tobacco ssu sequences were removed from plasmid 2018 by digestion with HindIII and SphI and ligated to HindIII/SphI digested pPMG72 (described in copending U.S. application Ser. No. 097,498, filed Sep. 16, 1987, which application is hereby incorporated by reference) to make pCGN650. pPMG72 contains the leader sequences of the soybean carboxylase attached to a modified aroA gene. In pCGN650 the soybean ssu leader is replaced by the tobacco ssu promoter and leader.

The aroA gene was replaced in pCGN650 by SphI-BamHI digestion and ligation with SphI-BamHI digested pCGN1303. The resulting plasmid, pCGN1304 now contains the tobacco ssu TSSU3-8 promoter and leader sequence and MnSOD coding region. A polyadenylation signal was added to EcoRI digested pCGN1304 by isolation and ligation of an EcoRI partial digest fragment from pCGN632. pCGN632 contains a 1.6 kb HaeIII fragment of TSSU3-2 (O'Neal et al, (1987) supra) adapted using SalI linkers into SalI digested pUC18. The entire HaeIII fragment includes 123 nucleotides of exon 2, intron 2, exon 3, the polyadenylation site and 1 kb#3' to the polyadenylation site of a tobacco ssu gene. The expression construct containing the tobacco ssu promoter and leader, the mutant MnSOD gene and tobacco ssu 3'-sequences is designated pCGN1305.

The MnSOD gene contained in the initial construct, pCGN1303, and the expression construct, pCGN1305, contain the entire MnSOD gene from the initial ATG codon (plus one extra amino acid) through the stop codon of the gene and 0.8 kb of bacterial 3' untranslated region. To eliminate a large part of the 3'-noncoding bacterial sequences in vitro mutagenesis was performed on pCGN1303 to insert a linker containing XbaI, BamHI and EcoRI restriction sites 18 nucleotides downstream of the stop codon. The 42 base oligonucleotide 5' ATACGCCTCATGAATTCGGATCCTCTAGAGCAGCAGGCGGC-3' was used to perform the mutagenesis and the resulting clone is pCGN1329. The long MnSOD sequence contained in the expression construct pCGN1305 was substituted with the shorter MnSOD sequence from the SphI site (at the ATG) to the new BamHI site downstream of the stop codon by SphI, BamHI digestion of pCGN1329 and ligation to pCGN1305 digested with SphI and BamHI to create pCGN1331. pCGN1331 was digested with HindIII to linearize the plasmid at the unique HindIII site at the 5' end of the tobacco ssu promoter and the entire plasmid was ligated to the HindIII digested binary vector pCGN783 to create the construct pCGN1332. (For the construction of pCGN783 see copending U.S. application Ser. No. 078,538, filed Jul. 28, 1987, which application is incorporated herein by reference). The binary vector includes the T-DNA borders (left border, LB and right border, RB) which delineate the DNA to be transferred into the plant, a bacterial marker, (gentamicin resistance), and a plant selectable marker that is co-transferred with the gene of interest, consisting of a kanamycin resistance gene expressed from the constitutive cauliflower mosaic virus 35S promoter and 3'-polyadenylation signal from transcript 7 of *agrobacterium* T-DNA. pCGN1331 can be cloned in either of two orientations at the HindIII site of pCGN783. pCGN1332 is in the orientation with the MnSOD gene and the kanamycin resistance gene being transcribed in opposite directions.

A second MnSOD expression construct in a binary vector was constructed. In this construct, pCGN1328, the MnSOD gene is expressed from the constitutive CaMV35s promoter and utilizes the soybean ssu leader for chloroplast targeting. pCGN1328 was constructed as follows: The mutagenized MnSOD gene in construct pCGN1303 was combined with the soybean ssu leader sequence by digestion with SphI and BamHI and ligation to pCGN350 digested with SphI and BamHI to make pCGN1306. Plasmid pCGN350 contains the leader sequence of the ssu of ribulose bisphosphate carboxylase from soybean and was constructed as follows: Plasmid pPMG70 (described in copending U.S. application Ser. No. 097,498, filed Sep. 16, 1987) was restricted with DdeI, blunted with Klenow fragment of DNA polymerase, digested with BamHI, and the ssu promoter fragment isolated. The fragment was cloned into pUC8 cut with SmaI-BamHI.

The soybean leader/MnSOD gene from pCGN1306 was cloned into the expression cassette pCGN986 (described below) by digestion with EcoRI, filling in the ends with DNA polymerase I and restricting with BamHI. The fragment was ligated to pCGN986 which had been digested with XbaI, filled in with DNA polymerase I and BamHI digested. Clones were isolated that contained both the regenerated XbaI and EcoRI sites from the ligation (pCGN1308a) and the clones which contained neither site (pCGN1308b).

pCGN986 contains a cauliflower mosaic virus 35S (CaMV35) promoter and a T-DNA tml 3'-region with multiple restriction sites between them. pCGN986 was derived from another cassette, pCGN206, containing a CaMV35S promoter and a different 3'-region, the CaMV region VI 3'-end. The CaMV 35S promoter was cloned as an AluI fragment (bp 7144–7734) (Gardner et al., *Nucl. Acids Res.* (1981) 9:2871–2888) into the HincII site of M13mp7 (Messing et al., *Nucl. Acids Res.* (1981) 9:309–321) to create C614. An EcoRI digest of C614 produced the EcoRI fragment from C614 containing the 35S promoter which was cloned into the EcoRI site of pUC8 (Vieira and Messing, *Gene* (1982) 19:259) to produce pCGN147.

pCGN148a containing a promoter region, selectable marker (KAN with 2 ATG's) and 3'-region, was prepared by digesting pCGN528 with BglII and inserting the BamHI-BglII promoter fragment from pCGN147. This fragment was cloned into the BglII site of pCGN528 so that the BglII site was proximal to the kanamycin gene of pCGN528.

The shuttle vector used for this construct pCGN528, was made as follows: pCGN525 was made by digesting a plasmid containing Tn5 which harbors a kanamycin gene (Jorgenson et al., *Mol. Gen. Genet.* (1979) 177:65) with HindIII-BamHI and inserting the HindIII-BamHI fragment containing the kanamycin gene into the HindIII-BamHI sites in the tetracycline gene of pACYC184 (Chang and Cohen, *J. Bacteriol.* (1978) 134: 1141–1156). pCGN526 was made by inserting the BamHI fragment 19 of pTiA6 (Thomashow et al., *Cell* (1980) 19:729–739), modified with XhoI linkers inserted into the SmaI site, into the BamHI site of pCGN525. pCGN528 was obtained by deleting the small XhoI fragment from pCGN526 by digesting with XhoI and religating.

pCGN149a was made by cloning the BamHI-kanamycin gene fragment from pMB9KanXXI into the BamHI site of pCGN148a. pMB9KanXXI is a pUC4K variant (Vieira and Messing, *Gene* (1982) 19:259–268) which has the XhoI site missing, but contains a functional kanamycin gene from Tn903 to allow for efficient selection in *agrobacterium*.

pCGN149a was digested with HindIII and BamHI and ligated to pUC8 digested with HindIII and BamHI to produce pCGN169. This removed the Tn903 kanamycin marker. pCGN565 and pCGN169 were both digested with HindIII and PstI and ligated to form pCGN203, a plasmid containing the CaMV 35S promoter and part of the 5'-end of the TN5 kanamycin gene (up to the PstI site, Jorgenson et al., (1979), supra). A 3'-regulatory region was added to pCGN203 from pCGN204 (an EcoRI fragment of CaMV (bp 408–6105) containing the region VI 3' cloned into pUC18 (Gardner et al., (1981), supra) by digestion with HindIII and PstI and ligation. The resulting cassette, pCGN206, was the basis for the construction of pCGN986.

The pTiA6 T-DNA tml 3'-sequences were subcloned from the Bam19 T-DNA fragment (Thomashow et al., (1980), supra) as a BamHI-EcoRI fragment (nucleotides 9062 to 12,823, numbering as in Barker et al., *Plant Mol. Biol.* (1982) 2:335–350) and combined with the pACYC184 (Chang and Cohen (1978), supra) origin of replication as an EcoRI-HindIII fragment and a gentamycin resistance marker (from plasmid pLB41), obtained from D. Figurski) as a BamHI-HindIII fragment to produce pCGN417.

The unique SmaI site of pCGN417 (nucleotide 11,207 of the Bam19 fragment) was changed to a SacI site using linkers and the BamHI-SacI fragment was subcloned into pCGN565 to give pCGN971. The BamHI site of pCGN971 was changed to an EcoRI site using linkers. The resulting EcoRI-SacI fragment containing the tml 3'regulatory sequences was joined to pCGN206 by digestion with EcoRI and SacI to give pCGN975. The small part of the Tn5 kanamycin resistance gene was deleted from the 3'-end of the CaMV 35S promoter by digestion with SalI and BglII, blunting the ends and ligation with SalI linkers. The final expression cassette pCGN986 contains the CaMV 35S promoter followed by two SalI sites, an XbaI site, BamHI, SmaI KpnI and the tml 3'-region (nucleotides 11207-9023 of the T-DNA).

The CaMV 35s expression construct with the soybean leader/MnSOD gene, pCGN1308b, was transferred into a chloramphenicol resistant (Cam$^r$) background by insertion into the chloramphenicol resistant vector, pCGN566, at the EcoRI and HindIII sites to create pCGN1312.

Similar to pCGN1305, the tobacco ssu/MnSOD expression construct, pCGN1312, contains the entire MnSOD gene and a long bacterial 3'-untranslated region. To remove much of the 3'-untranslated region, pCGN1312 was partially digested with BclI, completely digested with BamHI and religated.

The partial digestion was necessary because pCGN1312 contains 3 BclI sites, a BclI site in the coding region of the MnSOD clone, one in the 3'-untranslated region 95bp from the stop codon and one in the 3'-tml polyA fragment. A clone in which only the 3'-noncoding bacterial MnSOD BclI/BamHI fragment was identified by size and restriction pattern and named pCGN1322. pCGN1322 contains the entire MnSOD gene and only 95 nucleotides of 3'-noncoding sequence. pCGN1322 was cloned into the binary vector pCGN783 by digestion at the unique HindIII site and ligation to HindIII digested pCGN783. pCGN1328, the final binary vector, contains the MnSOD gene being transcribed in the same direction as the kanamycin resistant selectable marker.

The two binary vectors pCGN1328 and pCGN1332 were introduced into *Agrobacterium tumefaciens* strains LBA4404 (Ooms et al., *Plasmid* (1982) 7:15–29) and K61 (described below) respectively by transformation. A 10 ml culture of *agrobacterium* was grown overnight in MG/L broth (Garfinkel and Nester, *J. Bacteriol.* (1980) 144:732–743) at 30° C. and then diluted to 100 ml with MG/L broth and grown in a shaking incubator for 5 hours at 30° C. Cells were pelleted by centrifugation at 4,000 rpm for 10 minutes and the pellet resuspended in 1 ml MG/L and either placed on ice or frozen (−70° C.) in 200 µl aliquots.

Approximately 1µg of plasmid DNA (pCGN1328 or pCGN1332) in water or MG/L broth (about 100 µl) and 200 µl of competent *agrobacterium* cells were placed in a tube and immediately frozen in a dry ice-ethanol bath for 5 minutes. The tube was thawed in a 37° C. water bath for 5 minutes and 2 ml of MG/L broth was added to the cells. The culture was placed in a 30° C. shaking incubator for 3 hours. The cells were plated on MG/L containing 100 mg/l gentamicin. Plasmid DNA was isolated from individual gentamicin resistant colonies, transformed into *E. coli* and characterized by restriction enzyme analysis to verify that the gentamicin resistant EHA101 contained intact copies of pCGN1328 or pCGN1332.

EXAMPLE 5

MnSOD Construct For Cytoplasmic Targeting

The construction of a plasmid to express MnSOD in the cytoplasm was as follows: The MnSOD gene found in pCGN1329 (described above) was inserted into an ampicillin resistant background by digestion with HindIII and SphI and ligation to pUC18 digested with HindIII and SphI. The resulting plasmid, pCGN1363, was then digested with SalI and BamHI and ligated to pCGN1308a (described above) digested with SalI and BamHI to give pCGN1366. This replaced the soybean leader/MnSOD gene found in pCGN1308a with the shortened version of the MnSOD gene (with only 18 nucleotides of 3'-noncoding bacterial sequence). The MnSOD gene in pCGN1366 is flanked by the CaMV 35S promoter and the polyadenylation sequences of the tml gene of the T-DNA to make an expression cassette. The CaMV 35S promoter/MnSOD/tml 3'-sequences were moved to a chloramphenicol resistant background by digestion of pCGN1366 with HindIII and EcoRI and ligation to pCGN566 digest with EcoRI and HindIII to give pCGN1367. pCGN1367 was cloned into the binary vector pCGN783 at the unique HindIII site by digestion with HindIII and ligation to HindIII-digested pCGN783. The resulting binary vector, pCGN1371, contains the SOD transcription unit in the same orientation as the kanamycin transcription unit. pCGN1371 was transformed into *A. tumefaciens* strain K61 (as described below) to be cocultivated with tobacco leaf discs.

EXAMPLE 6

Construction of Disarmed Agrobacterium Strain K61
Construction of pCGN567

The left and right border regions of Ti plasmid pTiA6, Garfinkel, *J. Bact.* (1980) 144:732–743, were ligated together into pUC8. The resulting plasmid, pCGN503, has the left border region from bases 625-2212 and the right border from bases 13367–15298 (using the numbering system of Barker, et al.) fused in the proper orientation and flanked by HindIII sites. The HindIII fragment of pCGN503 was transferred to the broad host range cosmid pVCK102 Knauf, *Plasmid* (1982) 8:40–54, inactivating the kanamycin resistance locus of that plasmid and creating pCGN506. pCGN567 was made by ligating the kanamycin resistance locus from pUC4K Messing, *Gene* (1982) 19:269–272, into the unique BamHI site between the two border regions.
Final Construction of K61 pCGN567 was introduced into *agrobacterium* strain A722 (which contains pTiA6, Garfinkel, *J. Bact.* (1980) 144:732–743, by transformation, Holsters et al., *Mol. Gen. Genet.* (1978) and selection for kanamycin resistance. Plasmid pPH1J1, Hirsch, *Plasmid* (1984) 12:139–141 was introduced by conjugation, Ditta et al., *Proc. Nat'l. Acad. Sci.* (1980) 77:7347–7351, and *agrobacteria* were selected on gentamicin and kanamycin in minimal medium. Since pCGN567 and pPH1J1 are incompatible plasmids, selection for both markers results in very slow-growing colonies as the two plasmids tend to segregate to separate daughter cells. A double recombination event, which occurs at a low frequency between the homologous border regions of pCGN567 and pTiA6, results in the kanamycin resistance locus replacing the oncogenes of pTiA6. Since pTiA6 and pPH1J1 are compatible replicons, the pCGN567 recombinant containing pPH1J1 and the disarmed Ti plasmid grow relatively quickly under kanamycin and gentamicin selection. The construction of K61 is shown in FIG. 1.

Strain K61 may have been the result of a three step process as outlined in FIG. 1. Since the kanamycin resistance gene of pUC4K is homologous to the inactivated kanamycin resistance locus of PVCK102, an internal recombination in pCGN567 (D) would delete the right border region (E). Upon introduction of pPH1J1, the deleted plasmid could recombine with the left border region of pTiA6 (F) thus stabilizing the kanamycin resistance locus although the presence of the pCGN567 replicon in the recombinant pTiA6 would still destabilize pPH1J1 replication, slowing growth until a spontaneous deletion removed the pCGN567 replicon (G). In the case of strain K61, the spontaneous deletion apparently removed not only the incompatibility-coding portions of the cointegrate but also the oncogenes and adjacent regions. A deposit of strain K61 was made at the American Type Culture Collection on May 20, 1987 and assigned accession number ATCC 53621.

EXAMPLE 7

Transformation of Tobacco Plants

Transformation of tobacco plants was performed using *agrobacterium* containing constructs pCCN1328 and pCGN1332 as described in Comai et al., *Nature* (1985) 317:741–744, which publication is incorporated herein by reference.

EXAMPLE 8

Analysis of Transgenic Tobacco Plants for MnSOD Activity In the Chloroplast

When total leaf extracts were analyzed by Western Blot, plants transformed from either construct pCGN1328 or pCGN1332 showed a band corresponding to the size of properly processed MnSOD. Enzymes for processing the ssu transit peptide are found only in the chloroplast, as the presence of a properly processed MnSOD protein indicates that plants from construct pCGN1332 or 1328 have the enzyme in their chloroplast. Additional work was done, as discussed below, which further verified this finding.

Protocol for Isolation of Protoplasts

Leaves from plants transformed with pCGN1328, and leaves from untransformed plants for control, about two centimeters long and one centimeter across, were selected from 3–4 week old in vitro grown tobacco plants (var. xanthi). The midrib was dissected out and discarded. The remaining tissue was then placed in an enzyme solution (0.04% y23 pectolyase; 0.42% cellulase RS; 0.5% potassium dextran sulphate; 6% sorbitol; pH 5.5), approximately 15–20 leaves per 30 ml of enzyme solution. The tissue was infiltrated with the enzyme solution using vacuum to 300 millitorr. This was done by placing leaves and enzyme solution in a beaker, placing a screen on top of the leaves to prevent them from bubbling up while under vacuum, then placing the beaker in a desiccator and applying vacuum. The vacuum was then slowly released to atmospheric pressure.

The tissue with the enzyme solution was then transferred to petri dishes and placed in an orbital shaker at 50 rpm for 2 to 4 hours. Under magnification, the appearance of cellular rounding within the tissue and the releasing of protoplasts from the tissue was an indication that digestion was nearing completion. Using a 10 ml Japanese pipette, the tissue was slowly pipetted and agitated to further aid digestion. Tissue debris and undigested cells were then removed by passage through a 52 micron filter. The enzyme solution was removed by centrifugation at 150×g. The supernatant was discarded and the protoplast pellet rinsed with wash solution (0.5% potassium dextran sulfate; 6% sorbitol; pH 5.5) then centrifuged and the supernatant discarded. The washing step was repeated twice. The protoplasts were then counted using a hemocytometer. Test indicated that a minimum of 19 ml protoplast were needed to proceed with the analysis.

Chloroplast Isolation from Protoplasts

The protoplast suspension was passed through a 30 micron mesh screen attached to a 5 cc syringe until the protoplast were lysed. The suspension was then loaded onto a Percoll gradient, 15 ml 40% PBF-Percoll (3% polyethyleneglycol (PEG) 4000; 1% bovine serum albumin (BSA); 1% ficoll; in Percoll) over 6 ml 80% PBF-Percoll in a 30 ml Corex tube. The gradient was centrifuged in a swinging bucket rotor at 6000× g for 15 minutes. Chloroplast form into bands, one of broken chloroplasts near the top of the gradient, and a second of intact chloroplasts lower in the gradient. The broken band was removed and discarded. The intact band was transferred to a 50 ml culture tube. The intact chloroplasts were resuspended in 5–10 volumes of GR buffer (50 mM HEPES-KOH, pH 7.5; 0.33M sorbitol; 2.0 mM EDTA; 1.0 mM $MgCl_2$; 1.0 mM $MnCl_2$; 5.0 mM sodium ascorbate. The resuspended chloroplasts were then centrifuged at 1800 rpm in an IEC centrifuge for 80 seconds, starting timing at 1600 rpm. The supernatant was removed and the chloroplasts resuspended in 5–10 volumes of GR buffer. The centrifugation was then repeated and the chloroplasts resuspended in 2 ml sorbitol-HEPES (0.33M sorbitol; 50 mM HEPES-KOH, pH 7.5).

One half of each chloroplast preparation (1 ml) was subjected to digestion with protease (Trypsin, TPCK treated at 25 µg/ml for 45 minutes at 4° C.) to destroy proteins exterior to the chloroplast membrane. As a control, chloroplasts prepared from untransformed *N. Tabacum 'xanthi'* were "spiked" with purified MnSOD prior to protease treatment to verify the effectiveness of the treatment. The protease was diluted by addition of 30 volumes of sorbitol-HEPES. The digested chloroplasts were then washed twice with sorbitol-HEPES buffer.

Analysis of Chloroplasts for MnSOD by Western Blot

The chloroplasts were resuspended in 1 ml Western Extraction Buffer (WEB (100 mM sodium citrate, pH#5.6; 10 mM EDTA; 150 mM NaCl; 25 mg/ml (BSA); 0.05% Tween 20(polyoxyethylene sorbitan monolaurate; 2 mM phenylmethyl sulfonylfluoride (PMSF) dissolved in 100 ml ethanol before addition; 10 mM leupeptin; 10 mM; 10 mM dithiothreitol (DTT); 10 mM thiourea)) and homogenized using a Polytron, two bursts for five seconds at moderate speed to disrupt the chloroplasts. The samples were immunoprecipitated with 100 µl anti-MnSOD polyclonal antibody (1 mg/ml) and 250 µl Staphylococcus A cells overnight at 4° with shaking. The samples were then washed three times with TBST (10 mM Tris, pH 8.0; 150 mM NaCl; 0.05% Tween 20) and resuspended with 30 µl SDS-PAGE sample buffer (0.125M, Tris pH 6.8; 10% SDS; 20% Glycerol; 10% 2-β-mercaptoethanol (BME); Bromphenol Blue for color), boiled for three minutes and stored at 4° C. for 1–6 hours.

The samples were then loaded onto an 11% SDS-polyacrylamide gel with 5% stacking gel and electrophoresed at 50 volts (constant voltage) overnight (approximately 18 hours). The gel was electroblotted for three hours at 100 volts in Electroblot Buffer (For 6 Liters, 18.2 g Tris base; 86.5 g Glycine; 1200 mls methanol; to 6 L with distilled water). After blotting, the nitrocellulose was washed in distilled water and incubated in Blotto (20 mM Tris, pH 7.5; 5% dehydrated skim milk; 0.5M NaCl; 0.1% antifoam A; 10 mM sodium azide) for one hour at room temperature with gentle shaking. The nitrocellulose was then incubated in antibody/Blotto (anti-MnSOD polyclonal serum in Blotto 1:50, v/v) overnight at 4° C. with gentle shaking. The nitrocellulose was then washed for twenty minutes in TS buffer (20 mM Tris, pH 7.5; 150 mM NaCl), again for 20 minutes in T5 buffer plus 0.05% between 20, then again for 20 minutes in TS buffer. The nitrocellulose was then incubated for 2 hours at room temperature in Blotto +$^{125}$I-protein A (NEN Research Products, 0.5 µCi/ml Blotto) 100 ml, with gentle shaking. The nitrocellulose was then rinsed in approximately 100 ml of distilled water briefly, then incubated for four hours in Wash Buffer #1 (50 mM Tris, pH 7.5; 1M NaCl; 0.4% lauryl sarcosine) at room temperature with gentle shaking. The nitrocellulose was rinsed quickly in distilled water then dried under a heat lamp. Autoradiography was then performed for an appropriate time period. This analysis demonstrated the presence of properly processed E. coli MnSOD in the chloroplasts of transgenic plants transformed using construct 1328.

EXAMPLE 9

Analysis of SOD Activity in Transgenic Plants

Total leaf extracts from transgenic plants obtained from pCGN1328 were analyzed for SOD activity in a system of native gel electrophoresis followed by an SOD activity stain assay, capable of resolving total SOD activity into multiple component bands. MnSOD bands were then detected by binding to anti-MnSOD polyclonal antibody.

The activity stain assays were done as follows: Leaf samples were harvested and quick frozen using liquid nitrogen, then stored at −70° C. until use. 0.5 g of the frozen leaf tissue was then ground to a fine powder in a mortar and pestle pre-cooled with liquid nitrogen. Polyvinylpyrollidone (Polyclar AT) was then added to the ground samples (0.15 g/0.5g leaf tissue). Sodium citrate, 0.1M (pH 5.6) was then mixed in (750 µl/0.5 g leaf tissue). The samples were thawed and the tissue mixture transferred immediately to Corex centrifuge tubes and incubated on ice for 10 minutes. The samples were then centrifuged at 20,000×g for 15 minutes at 4° C. 120 µl of the supernatant was then removed from each sample and 20 µl of sucrose dye were added (25 g sucrose; 5 ml 1% Bromphenol Blue brought to 50 ml with distilled water; prepared fresh) and the samples electrophoresed on a native gel.

The solutions for the SOD activity stain for the native gel are as follows. Solution A: 30% acrylamide (acrylamide 58.4 g; bis acrylamide 1.6 g; brought to 200 ml); Solution B: 8× Laemmli resolving gel buffer (LRB) 3M Tris-HCl, pH 8.8; Solution C: 4× Laemmli stacking gel buffer (LSB), 0.5M Tris-HCl, pH 6.8); Solution D: 10× chamber buffer (0.25M Tris-HCl, pH 8.5; 1.92M glycine).

The gel was a 20×16×0.15×cm vertical slab. The resolving gel was a 10% acrylamide gel (11.7 mls acrylamide, 30:0.8); 4.38ml 8×LRB (pH 8.8); 18.8 ml water; 150 µl 10% APS, fresh (ammonium persulfate in water) 35 µl TEMED; brought to 35 ml. The gel was polymerized under n-butanol.

The stacking gel was a 6% acrylamide gel (4 ml acrylamide 30:08); 5 ml 4× LSB (pH 6.8); 10.7 ml water; 0.3ml APS (10%); 20µl TEMED.

The gel was run slowly (at about 5–6 mA) overnight at 4° C. The gel was then stained by immersion in activity stain (50 mM Tris, pH 8; 0.003% riboflavin; 2×10$^{-4}$M EDTA; 0.01% of nitro blue tetrazolium (NBT) and incubation for 30 min. in the dark with gentle shaking. The liquid was then poured off and the gel immediately illuminated with a bright light. When the spots were most intense, the gel was rinsed quickly with water and photographed.

The native gels for activity assay were then complexed with anti-MnSOD antibody as follows. The gels were soaked in 25 mM Tris-HCl pH 8.5, 0.192M glycine, 0.1% (w/v) SDS for 1.5 hours with gentle shaking. The gels were then electroblotted and hybridized as described above for the Western procedure.

An additional band of SOD activity, not present in wild-type N. Tabacum 'xanthi' plants, was detected in transformants by binding of the anti-MnSOD antibody after blotting. These data indicate that the E. coli MnSOD protein expressed in the transgenic tobacco plants is active.

EXAMPLE 10

Increased Drought Tolerance of Transgenic Tobacco Plants

Description of Genetic Material

Tobacco plant Xanthi-nc 1328-10-C was regenerated from cocultivation of Xanthi-nc leaf tissue with pCGN1328 using the leaf disk method and after selection on medium containing Kanamycin. Southern and Northern blot tests and a specific ELISA antibody test revealed that the novel MnSOD genetic sequences were integrated into the genome of regenerated T1 plants and that the corresponding mRNA and MnSOD protein were produced.

After selfing the T1 plant, T2 generation seeds were obtained and displayed a Mendelian segregation pattern when germinated on a medium containing Kanamycin, as shown in the Table I, suggesting that the new gene was integrated at a single locus.

TABLE 1

| | Transmission To Progeny[1] Of Kanamycin Resistance | | | | |
|---|---|---|---|---|---|
| Pollination Condition | Seeds Total | Non Germinated | Sensitive | Resistant | Segregation Ratio S:R |
| 1328-10-C | 200 | 14 | 40 | 146 | 1:3[2] |

[1]Seeds were surface sterilized and germinated under aseptic conditions on solid medium containing 100 mg/l kanamycin and incubated for 12 days under light.
[2]Chi-square analysis indicates observed values are reasonable for a 1:3 segregation ratio (sensitive:resistant) indicating a genotype of 1:2:1.

The T2 generation is a population of segregative plants composed of three groups of genotypes:

Group A: Genotype +,+; Homozygous resistant transformed Xanthi-nc (2 novel MnSOD gene doses)

Group B: Genotype +, −; Heterozygous resistant transformed Xanthi-nc (1 novel MnSOD gene doses )

Group C: Genotype −,−; Homozygous recessive transformed Xanthi-nc (No novel MnSOD gene)

If one assumes that no somaclonal variations have occurred during the regeneration process, all the above mentioned plants are considered as isolines: they display the same genetic background except the novel MnSOD gene.

Comparison of the different phenotypes may reveal the effect of the novel gene on the agronomic performances of the plants when cultivated under an environmental stress such as drought stress (hydric stress combined or not with heat stress). Overexpression of the Mn superoxide-dismutase enzyme in the transformed plants may contribute to a better protection of the photosynthetic apparatus from the negative action of the superoxide $O_2^-$ generated when plants are so stressed.

The resistance of the T2 plants to stress was tested as follows. T2 1328-10-C segregating plants were grown in the field under different drought stress treatments. Xanthi-nc wild type plants were also cultivated under the same conditions (group D, Xanthinc not transformed); treatments were applied at the same location. Three "environmental conditions" were used as follows: Environmental condition 1: "severe stress": plants were grown in an open field below a plastic field greenhouse; severe hydric and heat stresses were expected. Environmental condition 2: "natural stress": plants were grown in an open field. Local agro-climatic conditions indicated a high risk of drought stress from flowering to maturity stages. Environmental condition 3: "well watered": plants were grown in the open field, irrigation was scheduled in order to maintain the soil moisture profile at the field capacity.

Individual plants will be evaluated based upon the following characteristics: Total leaf number; Dates of beginning and completion of flowering stages; Date of senescence of specific organs; Height at maturity; Total biomass and fertility at harvest time.

ELISA tests performed on a subsample of T2 plants chosen at random will give an estimation of the content of the MnSOD protein in the plants. Progeny study on T3 seeds harvested on all the T2 plants will determine the corresponding genotypes.

EXAMPLE 11

Increased Metal Tolerance of Transgenic Tobacco Plants

Transgenic *N. Tabacum* Xanthi-nc transformed with pCGN1328 was obtained as described in Example 7 to provide transgenic plants 1328-4. Plants were grown in standard growth medium (Murashige and Skoog salts with 1 mg/l IAA and 1.5 mg/l kinetin). The standard growth medium contains 0.025 mg/l ($CuSO_4 \cdot 5H_2O$) and 8.6 mg/l $ZnSO_4 \cdot 7H_2O$. Prior to transfer to experimental medium, shoot tips were taken from the sterile-grown plants (3–4 weeks old), including 3–4 nodes. Leaves were removed, except from the meristems.

To evaluate the response of the transgenic plants to increasing concentrations of copper and zinc, the concentration of copper and zinc in standard growth medium was increased 10 fold, 20 fold, 40 fold, 60 fold or 100 fold the normal concentration. Each type of medium was adjusted to 0.7% Phytoagar. One hundred ml of medium were added to a 1 quart Mason jar which was covered with plastic food wrap and sterilized by autoclaving for 20 minutes. After the medium had cooled, the plantlets were added to the jars, 2 plants/jar in duplicate. As controls, non-transformed Xanthi-nc plants and plants transformed with a glyphosate resistance gene (aroA) were used.

The plants were grown at 25° C. with a 12 hour photoperiod. Light intensity during the photoperiod was 60–80 microeinsteins/m²/sec. Plants were evaluated 24 days after planting. At 40 fold the normal Cu/Zn concentration, the transgenic 1328 plants clearly outgrew the Xanthi-nc and transgenic aroA plants, as determined by visual observation of the height of the plants. The results are summarized in Table 2 below.

TABLE 2

| | Relative Growth of Plants Exposed to Increased Cu/Zn | | | | | |
|---|---|---|---|---|---|---|
| | Normal | Cu/Zn Concentration | | | | |
| Plant | Medium | 10x | 20x | 40x | 60x | 100x |
| SOD+ | ++++ | ++++ | ++++ | +++ | + | + |
| AroA | ++++ | ++++ | ++ | + | + | + |
| Xanthi-nc | ++++ | ++++ | +++ | ++ | + | + |

The above results demonstrate that plant species can be transformed efficiently with constructs which provide for expression of superoxide dismutase in a cell organelle such as a chloroplast. As evidenced by the above disclosure, plants are provided which have increased tolerance to environmental and chemical stresses such as drought and metal toxicity.

All publications and patent applications mentioned in this specification are indicative of the level of skill of those skilled in the art to which this invention pertains. All referenced publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for enhancing superoxide detoxification in a host plant, said method comprising:

transforming cells of said plant or parents of said cells, with an expression cassette, comprising a first DNA sequence encoding manganese superoxide dismutase which synthesizes manganese superoxide dismutase under the transcriptional and translational control of transcriptional and translational initiation and termination regulatory regions functional in said cells so that superoxide dismutase activity and superoxide detoxification by said plant is enhanced.

2. The method according to claim 1, wherein said expression cassette further comprises a second DNA sequence encoding a transit peptide joined in reading frame at the 5' terminus of said first DNA sequence so that transportation of said superoxide dismutase is directed to a plant cell organelle.

3. The method according to claim 2, wherein said plant cell organelle is a chloroplast.

4. The method according to claim 2, wherein said transit peptide is a tobacco or mature small subunit transit peptide.

5. The method according to claim 2, wherein said expression cassette further comprises a third DNA sequence encoding from about 10 to 20 post-processing amino acids of the N-terminus of a mature small subunit polypeptide joined in reading frame at the 3'-terminus of said second DNA sequence.

6. The method according to claim 5, wherein said mature small subunit polypeptide is a pea small subunit polypeptide.

7. The method according to claim 2, wherein said expression cassette further comprises a codon joined in reading frame at the 3'-terminus of said second DNA sequence.

8. The method according to claim 7, wherein said codon encodes glutamine.

9. A plant cell which produces superoxide dismutase at an enhanced level following exposure to stresses which increase superoxide, wherein said cell comprises:

at least one copy of a manganese superoxide dismutase gene, wherein said cell was obtained by transforming said cell, or a parent of said cell, with an expression cassette comprising a DNA sequence encoding superoxide dismutase under the control of transcriptional and translational initiation and termination regulatory regions functional in said cell.

10. A plant which produces increased levels of superoxide dismutase in response to a stress which increases superoxide, said plant comprising:

cells or progeny of cells transformed with a manganese superoxide dismutase gene so that functional expression of said gene by said cells increases the level of superoxide dismutase in response to stress.

11. The plant according to claim 10, wherein said stress is increased metal concentration in the rhizosphere.

12. The plant according to claim 11, wherein said metal is copper.

13. An expression cassette comprising: in the direction of transcription, transcriptional and translational initiation regions functional in a plant cell; a DNA sequence comprising a first sequence encoding a transit peptide in reading frame with a second sequence encoding manganese superoxide dismutase, wherein said transit peptide directs transport of said manganese superoxide dismutase to a cell organelle, and a transcriptional and translational termination region functional in said plant cell.

14. The expression cassette according to claim 13, wherein said DNA sequence further comprises a third sequence encoding about 10 to 20 post-processing amino acids of the N-terminus of a mature small subunit polypeptide joined in reading frame at the 3' terminus of said first sequence encoding a transit peptide.

15. The expression cassette according to claim 13, wherein said transcriptional initiation region comprises at least one cauliflower mosaic virus 35S transcriptional initiation region.

16. The expression cassette according to claim 15, wherein said transcriptional initiation region comprises two cauliflower mosaic virus 35S transcriptional initiation regions joined in tandem.

17. A DNA construct comprising:
an expression cassette according to claim 16 joined to sufficient T-DNA to provide for transfer and integration of said expression cassette into the genome of a plant cell.

18. A method for enhancing superoxide detoxification in a host plant, said method comprising:
transforming cells of said plant or parents of said cells, with an expression cassette, comprising a first DNA sequence encoding *Escherichia coli* manganese superoxide dismutase to synthesize manganese superoxide dismutase under the transcriptional and translational control of transcriptional and translational initiation and termination regulatory regions functional in said cells and a second DNA sequence encoding a transit peptide joined in reading frame at the 5' terminus of said first DNA sequence so that transportation of said manganese superoxide dismutase is directed to a plant cell chloroplast and so that superoxide dismutase activity and superoxide detoxification by said plant is enhanced.

19. The method according to claim 18, wherein said transit peptide is a tobacco or mature small subunit transit peptide.

20. The method according to claim 18, wherein said expression cassette further comprises a third DNA sequence encoding a single glutamine joined in reading frame at the 3'-terminus of said second DNA sequence.

21. The method according to claim 19, wherein said mature small subunit transit peptide is a pea small subunit polypeptide.

22. A plant cell which produces superoxide dismutase at an enhanced level following exposure to stresses which increase superoxide, wherein said cell comprises:
at least one copy of a manganese superoxide dismutase gene, wherein said cell was obtained by transforming said cell, or a parent of said cell, with an expression cassette comprising a first DNA sequence encoding *Escherichia coli* manganese superoxide dismutase under the control of a cauliflower mosaic virus 35S transcriptional initiation region and a transcriptional termination regulatory region and translational initiation and termination regulatory regions functional in said cell and a second DNA sequence encoding a small subunit transit peptide joined in reading frame at the 5' terminus of said first DNA sequence so that transportation of said superoxide dismutase is directed to a plant cell chloroplast and so that manganese superoxide dismutase production by said cell is increased in response to stress.

23. The plant cell according to claim 22, wherein said transcriptional initiation region is a tobacco small subunit transcription initiation regulatory region.

24. A plant producing increased levels of superoxide dismutase in response to a stress which increases superoxide, said plant comprising:
cells or progeny of cells transformed with an expression cassette comprising a first DNA sequence encoding *Escherichia coli* manganese superoxide dismutase under the control of a cauliflower mosaic virus 35S transcriptional initiation region and a transcriptional termination regulatory region and translational initiation and termination regulatory regions functional in said cell and a second DNA sequence encoding a small subunit transit peptide joined in reading frame at the 5' terminus of said first DNA sequence so that transportation of said superoxide dismutase is directed to a plant cell chloroplast and so that manganese superoxide dismutase production by said cell is increased in response to stress.

25. The plant according to claim 24, wherein said transcriptional initiation regulatory region is a tobacco small subunit transcriptional initiation regulatory region.

26. The plant according to claim 24, wherein said stress is increased metal concentration in the rhizosphere.

27. The plant according to claim 26, wherein said metal is copper.

28. An expression cassette comprising:
in the direction of transcription, transcriptional and translational initiation regions functional in a plant cell; a DNA sequence comprising a first sequence encoding a small subunit transit peptide in reading frame with a second sequence encoding *Escherichia coli* manganese superoxide dismutase, wherein said transit peptide directs transport of said superoxide dismutase to a plant cell chloroplast, and transcriptional and translational termination regions functional in said plant cell.

29. The expression cassette according to claim 28, wherein said DNA sequence further comprises a third sequence encoding a glutamine joined in reading frame at the 3' terminus of said transit peptide.

30. The expression cassette according a claim 28, wherein said transcriptional initiation region comprises at least one cauliflower mosaic virus 35S transcriptional initiation region.

31. The expression cassette according to claim 28, wherein said transcriptional initiation region comprises two cauliflower mosaic virus 35S transcriptional initiation regions joined in tandem.

32. The expression cassette according to claim 28, wherein said transcriptional initiation region comprises a tobacco small subunit transcriptional initiation region.

33. A DNA construct comprising:
an expression cassette according to claim 31 joined to sufficient T-DNA to provide for transfer and integration of said expression cassette into the genome of a plant cell.

* * * * *

UNITED STATES PATENT AND TRADEMARK OFFICE
CERTIFICATE OF CORRECTION

PATENT NO. : 5,538,878
DATED : July 23, 1996
INVENTOR(S) : Thomas, et al.

It is certified that error appears in the above-indentified patent and that said Letters Patent is hereby corrected as shown below:

Column 15, line 13, correct "pCCN" to --pCGN--.

Column 16, line 32, correct "pH#5.6" to --pH 5.6--; line 37, delete "10mM;" after leupeptin;.

Figure 1E:
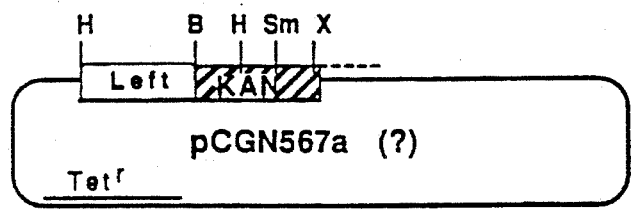
Figure 1F:
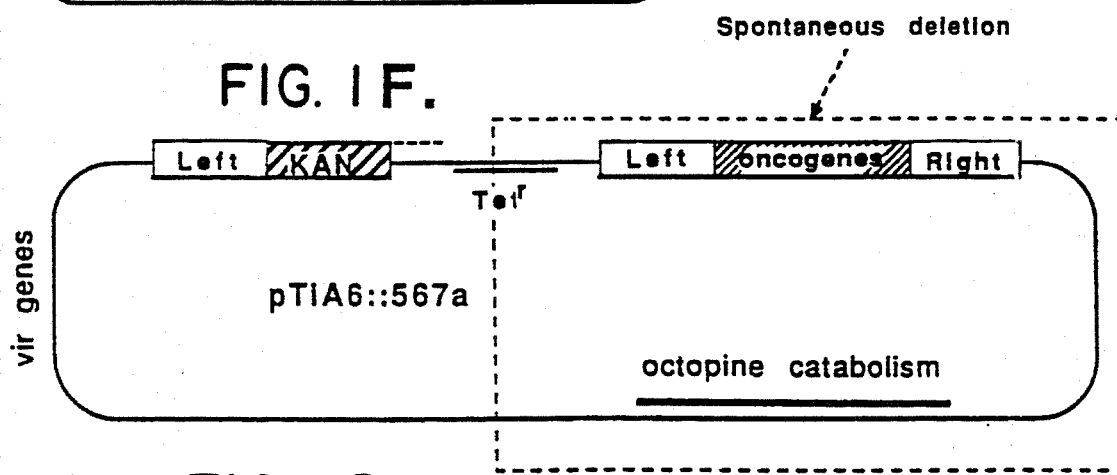
Figure 1G:
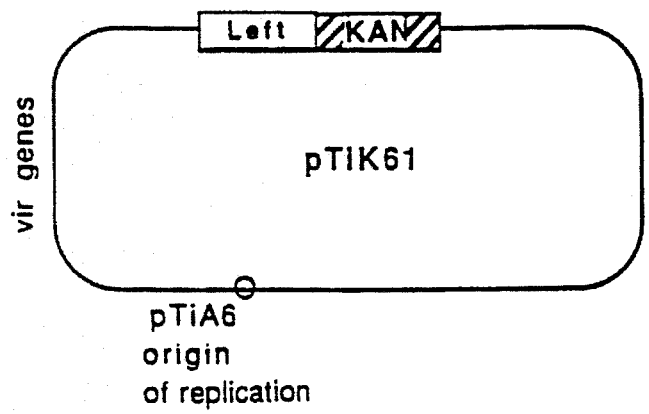

In the drawings, Fig 1A, text in hatched box, correct "onocgenes" to --oncogenes--; Fig. 1E, text in open area, delete "(?)".

Signed and Sealed this

Thirty-first Day of December, 1996

*Attest:*

BRUCE LEHMAN

*Attesting Officer*     *Commissioner of Patents and Trademarks*